(12) United States Patent
Beck et al.

(10) Patent No.: US 11,426,698 B2
(45) Date of Patent: Aug. 30, 2022

(54) DIFFUSION AND/OR FILTRATION DEVICE

(71) Applicant: GAMBRO LUNDIA AB, Lund (SE)

(72) Inventors: Christof Beck, Bitz (DE); Steffen Wagner, Messtetten (DE); Bernd Hertzler, Balingen (DE); Rainer Blickle, Bitz (DE); Stefan Ermantraut, Balingen (DE)

(73) Assignee: GAMBRO LUNDIA AB, Lund (SE)

( * ) Notice: Subject to any disclaimer, the term of this patent is extended or adjusted under 35 U.S.C. 154(b) by 641 days.

(21) Appl. No.: 16/326,449

(22) PCT Filed: Aug. 30, 2017

(86) PCT No.: PCT/EP2017/071700
§ 371 (c)(1),
(2) Date: Feb. 19, 2019

(87) PCT Pub. No.: WO2018/041858
PCT Pub. Date: Mar. 8, 2018

(65) Prior Publication Data
US 2021/0283553 A1 Sep. 16, 2021

(30) Foreign Application Priority Data
Aug. 31, 2016 (EP) .................................. 16186583

(51) Int. Cl.
B01D 63/02 (2006.01)
A61M 1/16 (2006.01)
(Continued)

(52) U.S. Cl.
CPC ......... *B01D 63/021* (2013.01); *A61M 1/1621* (2014.02); *B01D 61/14* (2013.01);
(Continued)

(58) Field of Classification Search
CPC .............. B01D 63/021; B01D 2313/04; B01D 2313/20; B01D 2313/21; B01D 2313/44; B01D 61/14; B01D 61/28; A61M 1/1621
See application file for complete search history.

(56) References Cited

U.S. PATENT DOCUMENTS 4,031,012 A * 6/1977 Gics .................... B01D 63/024
210/321.81
4,283,284 A 8/1981 Schnell
(Continued)

FOREIGN PATENT DOCUMENTS

EP 0 305 687 A1 3/1989
EP 0706818 4/1996
(Continued)

OTHER PUBLICATIONS

JP 2005161305A, machine translation.*
(Continued)

Primary Examiner — Benjamin L Lebron
(74) Attorney, Agent, or Firm — Barnes & Thornburg LLP

(57) ABSTRACT

The present disclosure relates to diffusion and/or filtration devices comprising hollow fiber membranes, e.g., ultrafilters for water purification, plasma filters, or capillary dialyzers for blood purification; housings and end caps for the devices; and methods for the production of the devices.

12 Claims, 3 Drawing Sheets

(51) Int. Cl.
*B01D 61/14* (2006.01)
*B01D 61/28* (2006.01)

(52) U.S. Cl.
CPC .......... *B01D 61/28* (2013.01); *B01D 2313/04* (2013.01); *B01D 2313/20* (2013.01); *B01D 2313/21* (2013.01); *B01D 2313/44* (2013.01)

(56) References Cited

U.S. PATENT DOCUMENTS

| | | |
|---|---|---|
| 4,414,110 A | 11/1983 | Geel et al. |
| 4,497,104 A | 2/1985 | Fowles et al. |
| 4,708,796 A | 11/1987 | Yoshimoto et al. |
| 5,192,499 A | 3/1993 | Sakai et al. |
| 5,472,601 A | 12/1995 | Eguchi |
| 2003/0080047 A1 | 5/2003 | Watkins et al. |
| 2005/0194305 A1 | 9/2005 | Vido et al. |

FOREIGN PATENT DOCUMENTS

| | | | |
|---|---|---|---|
| EP | 0844015 | 5/1998 | |
| EP | 2832423 | 2/2015 | |
| JP | 2005-161305 | 6/2005 | |
| JP | 2014226607 A | * 12/2014 | |
| WO | WO-8402478 A1 | * 7/1984 | ............ B01D 63/02 |
| WO | WO 01/60477 A2 | 8/2001 | |
| WO | WO2013/190022 | 12/2013 | |

OTHER PUBLICATIONS

Machine translation of JP 2014 226607, Nov. 18. (Year: 2021).*
PCT Search Report and Written Opinion prepared for PCT/EP2017/071700, completed Nov. 8, 2017.

* cited by examiner

DIFFUSION AND/OR FILTRATION DEVICE

CROSS-REFERENCE TO RELATED APPLICATIONS

This application is the U.S. national phase of PCT/EP2017/071700, filed on Aug. 30, 2017, which claims the benefit of European Patent Application Serial Number 16186583.7, filed on Aug. 31, 2016, the entire disclosures of both of which are incorporated herein by reference.

TECHNICAL FIELD

The present disclosure relates to diffusion and/or filtration devices comprising hollow fiber membranes, e.g., ultrafilters for water purification, plasma filters, or capillary dialyzers for blood purification; housings and end caps for the devices; and methods for the production of the devices.

BACKGROUND OF THE INVENTION

Diffusion and/or filtration devices comprising hollow fiber membranes are widely used for separation or purification of liquids. Examples are ultrafilters used for water purification; plasma filters for the separation of plasma from blood; capillary dialyzers for blood purification in patients suffering from renal insufficiency, i.e., for treatment of the patients by hemodialysis, hemodiafiltration or hemofiltration; etc. A multitude of different models of diffusion and/or filtration devices comprising hollow fiber membranes is commercially available.

The devices generally consist of a housing comprising a tubular section with end caps capping the mouths of the tubular section. A bundle of hollow fiber membranes is arranged in the housing in a way that a seal is provided between a first flow space formed by the fiber cavities and a second flow space surrounding the membranes on the outside. The seal generally is provided by end wall means within the housing formed by a polymer mass in which the ends of the hollow fiber membranes are embedded. Examples of such devices are disclosed in EP 0 844 015 A2, EP 0 305 687 A1, WO 01/60477 A2, and WO 2013/190022 A1.

It is important that the seal between the end caps and the housing and the seal between the flow space formed by the fiber cavities and the flow space surrounding the membranes on the outside remain intact at all times, especially during operation of the device. Often, additional parts like sealing rings, gaskets, and support rings are provided in the device as additional safeguards against leakage. Production, handling, and subsequent assembly of the additional elements add to the complexity of the production process and the manufacturing cost. It would therefore be desirable to dispense with these additional parts in the device.

To this end, it is imperative that a tight connection between the end walls and the inner surface of the dialyzer housing is established and any delamination is prevented. The end walls and the housing of the device generally are comprised of different materials which also usually have different thermal expansion coefficients. As a consequence, temperature changes during manufacture or processing of the device, e.g. thermal sterilization, or pressure changes within the device during operation generate strain at the interface between the inner wall of the housing and the end wall means which may cause delamination of the end wall means from the housing and generate leaks. This is particularly the case for combinations of materials where the adhesive force between the respective materials is low, for instance, when a polypropylene housing is combined with polyurethane end wall means. Likewise, the seal between the housing and the end caps must remain intact at all times to prevent fluid leaks.

SUMMARY OF THE INVENTION

The present application relates to a diffusion and/or filtration device which does not comprise sealing rings, gaskets, or support rings. The device comprises a housing and end caps of optimized construction. Processes for the production of the device also are provided.

SHORT DESCRIPTION OF THE DRAWINGS

DETAILED DESCRIPTION

Figure 1:
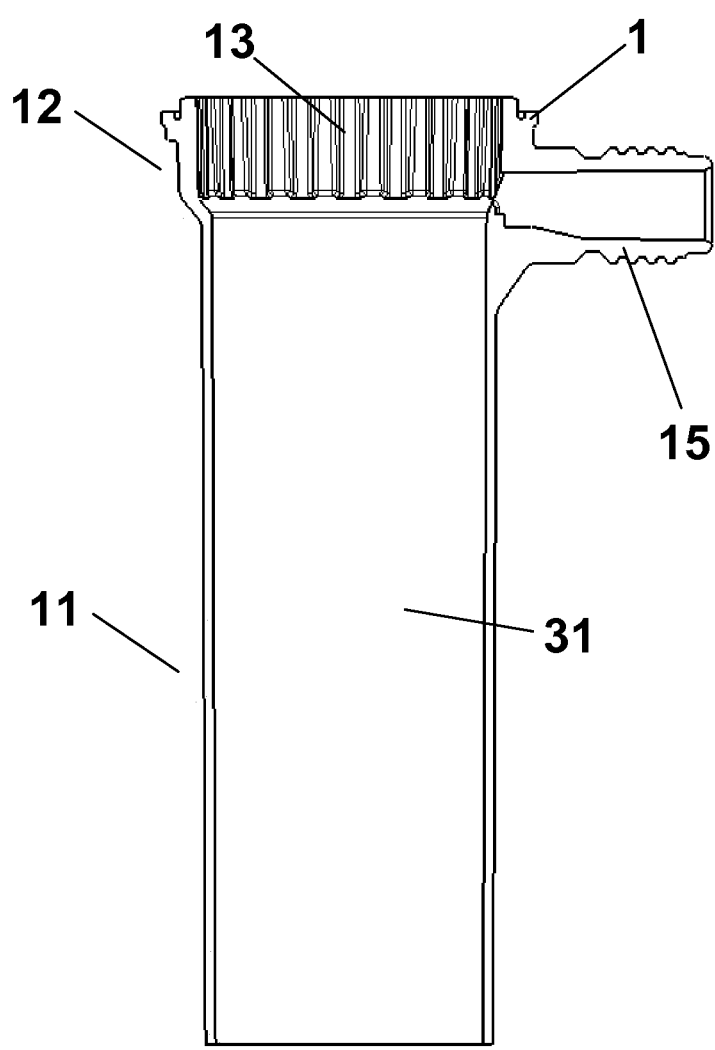
FIG. 1 shows a longitudinal-sectional partial view and a top view of an embodiment of the dialyzer housing of the present disclosure.
Figure 1:
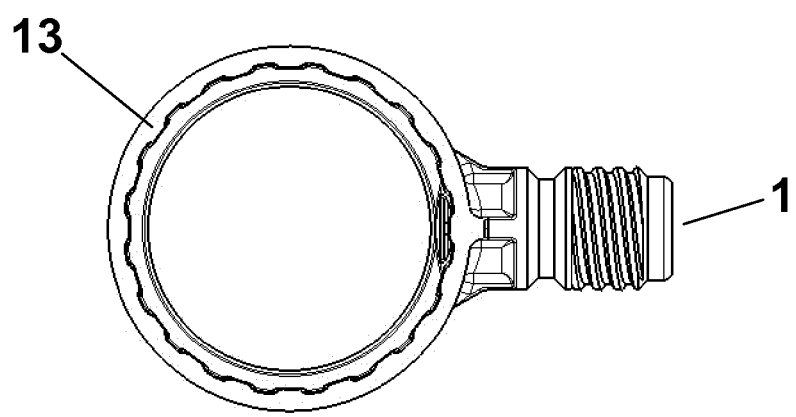
Figure 2:
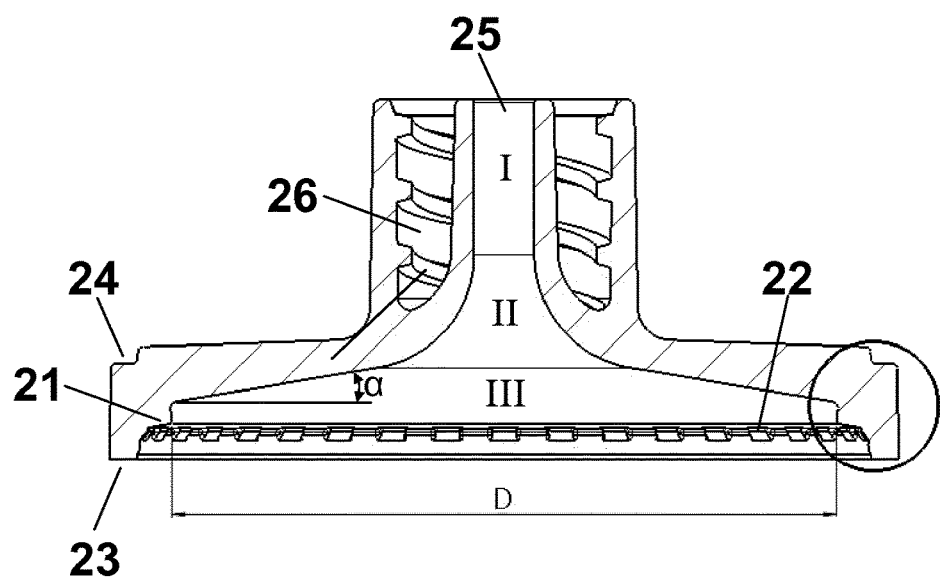
FIG. 2 shows a longitudinal-sectional schematic view of an embodiment of the dialyzer end cap of the present disclosure.
Figure 2:
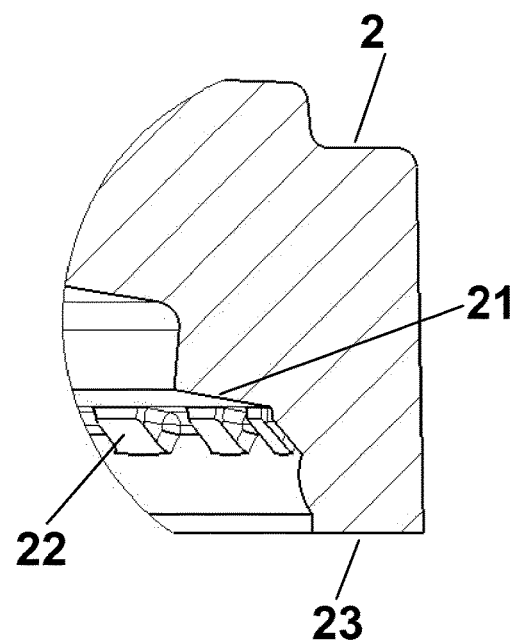

A housing 10 for a diffusion and/or filtration device 30 is provided. The housing 10 comprises a tubular midsection 11 and header sections 12 at both ends of the tubular midsection 11. The header sections 12 have a diameter which is larger than the diameter of the tubular midsection 11. In one embodiment, the inner diameter of the tubular midsection 11 is in the range of from 20 mm to 55 mm, for instance 25 to 50 mm. The difference of the diameters of the tubular midsection 11 and the header sections 12 generally is in the range of from 5 mm to 15 mm, e.g., 5 to 10 mm.

The wall strength of the header sections 12 is greater than the wall strength of the tubular midsection 11. In one embodiment of the housing 10, the wall strength of the header sections 12 is in the range of from 2 to 3 mm.

A plurality of elongated noses 13 is arranged on the inside surface of each header section 12. The noses 13 run parallel to the longitudinal axis of the housing 10 and parallel to each other. In one embodiment of the housing 10, the noses 13 are evenly spaced over the circumference of the inner surface of each header section 12. In one embodiment of the housing 10, the number of noses 13 in each header section 12 is in the range of from 15 to 25. In the embodiment shown in FIG. 1, each header section 12 comprises 20 noses. In one embodiment of the housing 10, each nose 13 has a width in the range of from 3 to 4 mm, e.g., 3.3 to 3.7 mm. In one embodiment of the housing 10, each nose 13 has a length in the range of from 10 to 15 mm, for instance, 12 to 14 mm. In one embodiment of the housing 10, each nose 13 has a height in the range of from 0.5 to 1.0 mm, for instance, 0.6 to 0.8 mm.

In one embodiment of the housing 10, the header sections 12 each comprise a collar 14. The collar 14 has a diameter which is larger than the diameter of the header section 12. As shown in FIG. 1, the upper rim of the collar 14 defines a gap to the outside surface of the header section 12; and it is positioned below the upper rim of the header section 12. In one embodiment of the housing 10, the gap between the outer surface of the header section 12 and the upper rim of the collar 14 has a width in the range of from 0.5 to 1.0 mm, for instance 0.6 to 0.8 mm. In one embodiment of the housing 10, the upper rim of the collar 14 is planar. In one embodiment of the housing, the upper rim of the collar 14 has a wall strength in the range of from 1.5 to 2.0 mm, for instance, 1.6 to 1.8 mm.

The housing 10 comprises one or two fluid ports 15. The fluid port(s) 15 serve(s) as an inlet or an outlet, respectively, for a liquid.

The housing 10 is comprised of a transparent or opaque polymeric material. Examples of suitable polymeric materials include polymethyl(meth)acrylate (PMMA); polyesters like PET or PBT; and polycarbonate. In one embodiment, the housing 10 is comprised of a polyolefin. Examples of suitable polyolefins are polyethylene, polypropylene, polybutylene, polystyrene (HIPS), and cycloolefin copolymers (COC). In one embodiment, the housing 10 is comprised of polypropylene.

An end cap 20 for a diffusion and/or filtration device 30 also is provided. The end cap 20 has an inner surface which is axially symmetrical with regard to the longitudinal axis of the end cap 20 and has an inner surface having the form of a funnel and comprises, in the direction of increasing diameter, a first section I taking the form of a cylinder or a truncated cone, a middle section II taking the form of a torus segment, and a third section III taking the form of a truncated cone.

The end cap 20 comprises a fluid port 25, which is an inlet or outlet, respectively, for a liquid, arranged axially in the center of the end cap 20. In one embodiment of the end cap 20, a two-start thread which fits a standard blood-line connector is provided round the fluid port 25. Starting from the mouth of the end cap 20, the inner diameter of the fluid port 25 is constant or increases linearly in a first section I of the end cap, then widens gradually, with a constant curvature R, in a second section II until the inner surface includes a predetermined angle α with the horizontal. The diameter then increases linearly in a third section III, until a predetermined diameter D is reached.

In one embodiment, the radius R of the middle section II, i.e., the curvature R, is in the range of from 4 mm to 10 mm, e.g., from 5 mm to 9 mm, in particular from 6 to 8 mm. In one embodiment, the aperture of the first section I from the inlet to the middle section is in the range of from 0° to 4°, e.g., from 1° to 3°, in particular from 1.5 to 2.5°. In one embodiment, the angle α is in the range of from 7 to 12°, i.e. the aperture of the third section III is in the range of from 156 to 166°. The diameter D generally is in the range of from to 20 to 60 mm, e.g., 30 to 50 mm.

The end cap 20 comprises a circumferential planar sealing face 21 sloping at an angle in the range of from 5° to 10°. In one embodiment of the end cap 20, the sealing face 21 has a width in the range of from 1.5 to 2.5 mm.

In one embodiment, the end cap 20 comprises a plurality of noses 22 evenly distributed over an annulus of the inner surface of the end cap 20. The annulus has an inner diameter which is larger than the outer diameter of the sealing face 21. In one embodiment, the number of noses 22 is in the range of from 30 to 50, for instance, 35 to 45. In one embodiment of the end cap 20, the width of each nose 22 is in the range of from 1.0 to 2.0 mm, for instance, 1.3 to 1.7 mm. In one embodiment of the end cap 20, the height of each nose 22 is in the range of from 0.25 to 0.75 mm, e.g., 0.4 to 0.6 mm. In one embodiment of the end cap 20, the distance between vicinal noses 22 is in the range of from 1.5 to 2.5 mm, for instance, 1.8 to 2.2 mm.

In one embodiment of the end cap 20, the wall strength of the end cap 20 in the zone of the third section III increases towards the periphery of the end cap 20. In one embodiment, the ratio of the wall strength at the outer diameter of section III to the wall strength at the inner diameter of section III is in the range of from 2:1 to 5:1, for instance, 2:1 to 3:1.

In one embodiment of the end cap 20, the width of the outer rim 23 of the end cap 20 is in the range of from 1.5 to 2.0 mm, for instance, 1.6 to 1.8 mm. In one embodiment, the outer rim 23 of the end cap 20 is planar and the plane is perpendicular to the longitudinal axis of the end cap 20.

In one embodiment, the end cap 20 comprises an annular plane 24 running along the circumference of the end cap 20 on its upper side. The annular plane 24 is perpendicular to the longitudinal axis of the end cap 20. In one embodiment of the end cap 20, the width of the annular plane 24 is equal to the width of the outer rim 23 of the end cap 20.

The end cap 20 is comprised of a transparent or opaque polymeric material. Examples of suitable polymeric materials include polymethyl(meth)acrylate (PMMA); polyesters like PET or PBT; and polycarbonate. In one embodiment, the end cap 20 is comprised of a polyolefin. Examples of suitable polyolefins are polyethylene, polypropylene, polybutylene, polystyrene (HIPS), and cycloolefin copolymers (COC). In one embodiment, the end cap 20 is comprised of polypropylene.

A diffusion and/or filtration device 30 also is provided, which comprises a housing 10 and end caps 20 as described above. In one embodiment, the diffusion and/or filtration device 30 comprises a housing 10 as described above, defining a longitudinally extending internal chamber 31 including a first end and a second end. It further comprises a bundle 32 of semi-permeable hollow fiber membranes disposed within the internal chamber 31 and extending longitudinally from the first end of the internal chamber 31 to the second end of the internal chamber 31, the hollow fiber membranes each having an outer surface, and a first end and a second end corresponding to the first end and the second end of the internal chamber 31. The device features end wall means 33 supporting the first and second ends of the hollow fiber membranes within the internal chamber 31 so as to sealingly separate the first ends and second ends of the hollow fiber membranes from the outer surfaces of the hollow fiber membranes between the first ends and second ends thereof. End caps 20 as described above seal the mouths of the housing 10. The device comprises one or two fluid ports 15 arranged on the housing 10 at a position between the end wall means 33 supporting the first and second ends of the hollow fiber membranes. The fluid port(s) 15 serve(s) as an inlet or an outlet, respectively, for a liquid.

Figure 3:
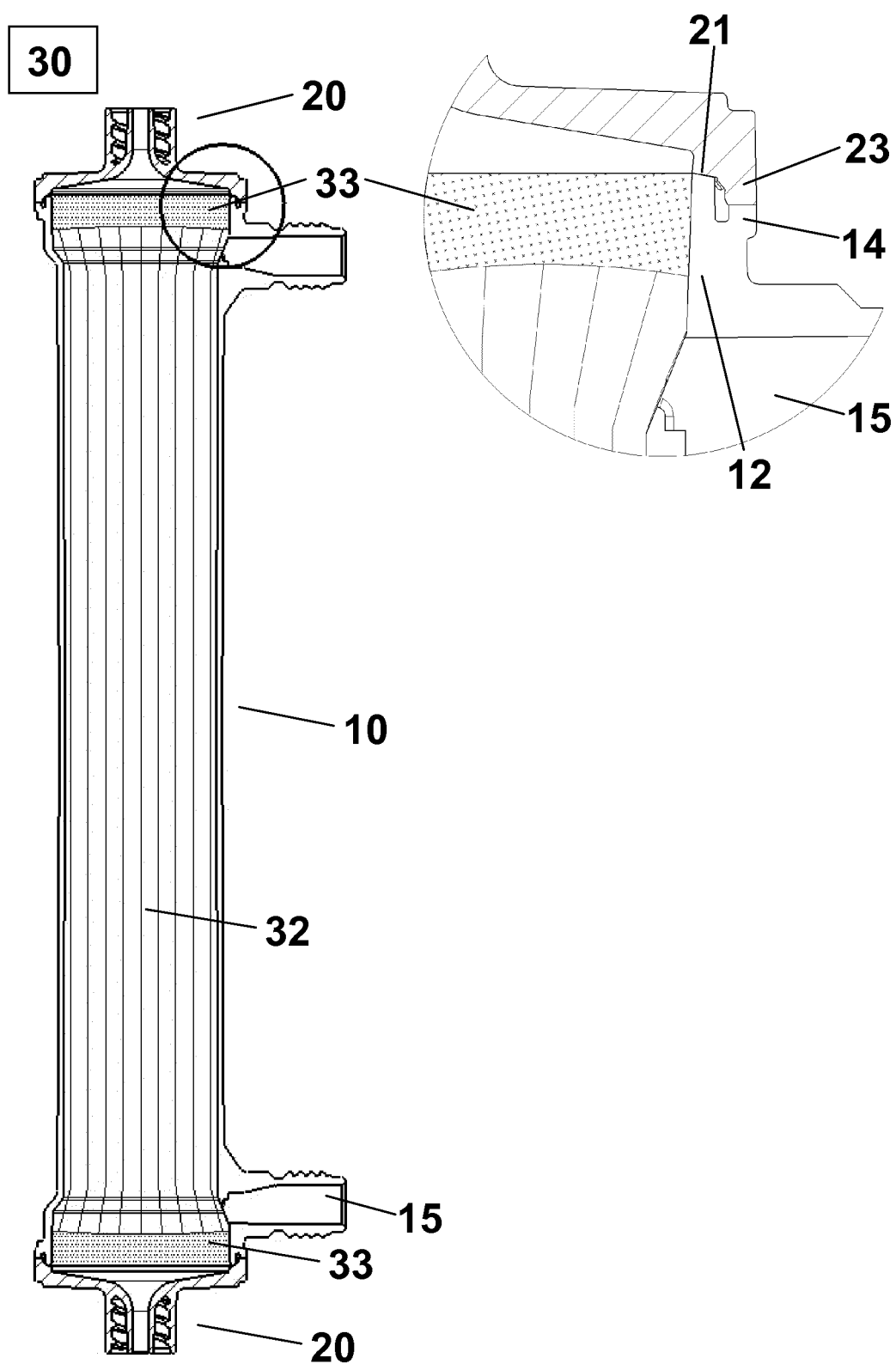
FIG. 3 shows a longitudinal-sectional schematic view of an embodiment of the diffusion and/or filtration device of the present disclosure.

In one embodiment of the diffusion and/or filtration device 30, the upper rim of each header section 12 of the housing 10 slopes at the same angle as the circumferential planar sealing face 21 of the end cap 20. The upper rim of the header section 12 of the housing 10 and the circumferential planar sealing face 21 of the end cap 20 contact each other and form a first tight seal. The outer rim 23 of the end cap 20 is fused to the housing 10 and provides a second tight seal. In one embodiment of the diffusion and/or filtration device 30 shown in FIG. 3, the outer rim 23 of the end cap 20 is fused to the upper rim of the collar 14 of the housing 10 to provide the second tight seal.

The present disclosure also provides a process for producing the diffusion and/or filtration device 30. The process comprises the following steps:
  a) providing a housing 10 as described above, defining a longitudinally extending internal chamber 31 including a first end and a second end;

b) introducing a bundle 32 of semi-permeable hollow fiber membranes each having an outer surface, a first end and a second end into the internal chamber 31 of the housing 10 so that the bundle 32 extends longitudinally from the first end of the internal chamber 31 to the second end of the internal chamber 31 and the first ends and second ends of the hollow fiber membranes correspond to the first end and the second end of the internal chamber 31, respectively;

c) providing end wall means 33 supporting the first and second ends of the hollow fiber membranes within the internal chamber 31 so as to sealingly separate the first ends and second ends of the hollow fiber membranes from the outer surface of the hollow fiber membranes between the first ends and second ends thereof, by introducing a potting material into the header sections 12 of the housing 10 and allowing the potting material to cure;

d) opening the first and second ends of the hollow fiber membranes by cutting through the end wall means 33 perpendicularly to the longitudinal axis of the housing 10;

e) providing an end cap 20 as described above for each header section 12;

f) circumferentially beveling the wall of the rim of each header section 12 to produce a rim of the header section 12 which slopes at an angle matching the slope of the circumferential planar sealing face 21 of the end cap 20;

g1) closing each header section 12 with an end cap 20, thereby causing the rim of the header section 12 of the housing 10 and the circumferential planar sealing face 21 of the end cap 20 to contact each other and form a first tight seal; and g2) fusing each end cap 20 to the housing 10, thereby providing a second tight seal.

A bundle 32 of semi-permeable hollow fiber membranes is introduced into the internal chamber 31 of the housing 10. Each hollow fiber membrane has an outer surface, a first end and a second end. After the bundle 32 has been inserted into the housing 10, the bundle 32 extends longitudinally from the first end of the internal chamber 31 to the second end of the internal chamber 31; and the first ends and second ends of the hollow fiber membranes correspond to the first end and the second end of the internal chamber 31, respectively.

It is expedient to close the ends of the hollow fiber membranes before the subsequent potting step in order to prevent the potting material from permeating into the fibers. The fiber ends can be closed by processes known in the art, e.g., by melting or by means of an adhesive. In one embodiment of the process, the ends of the hollow fiber membranes are closed before the bundle 32 of hollow fiber membranes is introduced into the housing 10.

The end wall means 33 supporting the first and second ends of the hollow fiber membranes within the internal chamber 31 are generated by potting the ends of the hollow fiber membranes with a polymer. A suitable potting material for the hollow fiber membranes is polyurethane. In an exemplary process, the ends of the housing 10 are closed and potting material, for instance polyurethane, is introduced into the housing 10 via at least one fluid port 15. The potting material is distributed within the housing 10 of the diffusion and/or filtration device 30 by centrifugation, i.e., rotating the diffusion and/or filtration device 30 at high speed perpendicular to its longitudinal axis. The potting material is allowed to cure; thereby forming end wall means 33 on both ends of the bundle 32 of hollow fiber membranes.

The potting material shrinks during the curing process. The shrinkage of the cross-section of the end wall means 33 generates a centripetal tensile force on the header section 12 of the housing 10. The noses 13 provide an additional lock between the end wall means 33 and the housing 10. It prevents detachment of the end wall means 33 from the inner wall of the housing 10 and thus the formation of leaks.

The ends of the hollow fiber membranes are subsequently opened by cutting through the end wall means 33 perpendicularly to the longitudinal axis of the housing 10. Part of the end wall means 33 and the header sections 12 of the housing 10 are thus removed, producing a planar cut face perpendicular to the longitudinal axis of the housing 10.

The wall of the rim of each header section 12 is subsequently beveled circumferentially to produce a rim of the header section 12 which slopes at an angle matching the slope of the circumferential planar sealing face 21 of the end cap 20. The beveled rim is smooth and even and also represents a circumferential planar sealing face. In one embodiment, a rotating blade is used to bevel the rim of each header section 12. The blade rotates around the longitudinal axis of the housing 10 and includes an angle with the longitudinal axis of the housing 10 that matches the desired slope of the rim, i.e. the blade includes an angle of 80 to 85° with the longitudinal axis. The rotating blade is moved towards the housing 10 along the longitudinal axis of the housing 10 until the rim of the header section 12 has been beveled. The housing 10 then is turned around and the rim of the header section 12 on the other end of the housing 10 is beveled similarly. An advantage of the design of the diffusion and/or filtration device 30 of the present disclosure which includes a beveled rim of the header sections 12 is that a smooth and even sealing face can be produced on the rim of the header sections 12 without compromising the planar cut face of the end wall means 33 generated in the previous process step, and without generating discontinuities, i.e. steps, between the end wall means 33 and the housing 10.

After the beveling step, the header sections 12 are closed with end caps 20, thereby causing the rim of the respective header section 12 of the housing 10 and the circumferential planar sealing face 21 of the corresponding end cap 20 to contact each other and form a first tight seal. The particular design of the diffusion and/or filtration device 30 of the present disclosure which includes a circumferential planar sealing face 21 in the end cap 20 and a matching rim of the header section 12 of the housing 10 which also represents a circumferential planar sealing face, both sealing faces sloping at the same angle, makes it possible to provide a fluid-tight seal between the end cap 20 and the housing 10 without having to resort to additional elements like sealing rings, gaskets, or support rings. In addition to the benefit of having fewer components, the space otherwise required by the additional elements now can be utilized, i.e., a larger proportion of the face of the end wall means 33 is accessible to a fluid. This also allows for an increased diameter of the bundle 32 of hollow fiber membranes in the header section 12.

The end caps 20 then are fused to the housing 10, thereby providing a second tight seal. In one embodiment of the process, the second tight seal is provided by fusing the outer rim 23 of the end cap 20 to the upper rim of the corresponding collar 14 of the housing 10.

In one embodiment of the process, first one header section 12 of the housing 10 is sealed with an end cap 20, and then the other. In another embodiment of the process, both header sections are simultaneously sealed with end caps 20.

In one embodiment of the process, a contact force is applied to the upper side of the end cap 20 in the direction of the longitudinal axis of the housing 10, after the header section 12 has been closed with the end cap 20, thereby pressing the circumferential planar sealing face 21 of the end cap 20 onto the upper rim of the corresponding header section 12 of the housing 10. The contact force is maintained until the end cap 20 has been fused to the housing 10. In one embodiment, the contact force is applied to an annular plane 24 which runs along the circumference of the end cap 20 on its upper side. The annular plane 24 is perpendicular to the longitudinal axis of the end cap 20. In one embodiment, the width of the annular plane 24 equals the width of the outer rim 23 of the end cap 20; and the outer rim 23 of the end cap 20 and the annular plane 24 are congruent. In one embodiment, the contact force is in the range of from 3,000 to 5,000 N, for instance, 3,500 to 4,500 N.

The noses 13 and the increased wall strength of the header sections 12 increase the rigidity of the header sections 12, making them less prone to deformation. Likewise, the profile of section III of the end cap 20, with its wall strength increasing in radial direction towards the outer diameter of the end cap 20, and the noses 22 in the end cap 20, which are positioned adjacent to the outer diameter of the sealing face 21, increase the rigidity of the end cap 20 and make it less prone to deformation. As a result, when the end cap 20 is placed on the header section 12 of the housing 10, an accurate fit is achieved between the sealing face 21 of the end cap 20 and the rim of the header section 12, thus providing a fluid-tight seal. Additionally, when a contact force is applied to the end cap 20, and in particular to the annular plane 24, the contact force does not cause a deformation of the end cap 20 or the header section 12 which would weaken the seal formed by the sealing face 21 of the end cap 20 and the rim of the header section 12. Instead, the contact force applied presses together the sealing face 21 of the end cap 20 and the rim of the header section 12 of the housing 10, and enhances the adhesive strength of the seal.

A variety of techniques known in the art can be used to fuse the end caps 20 to the housing 10. Suitable examples include laser welding, ultrasonic welding, friction welding, electron beam welding, and solvent welding. The end caps can also be glued to the housing with an adhesive for instance, a polyurethane adhesive. In one embodiment of the process, the end cap 20 is fused to the housing 10 using hot plate welding. A hot plate is brought into close vicinity of the parts to be fused together. After a time sufficient to melt the corresponding parts of the end cap 20 and the housing 10, respectively, to be fused, the hot plate is removed and the end cap 20 and the housing 10 are pressed together until the melt has solidified, thereby forming a tight seal between the end cap 20 and the housing 10. The temperature of the hot plate generally is in the range of from 200 to 400° C. Exemplary processes use temperatures in the range of from 220 to 240° C.; or from 330 to 380° C., respectively. The time required to partially melt the components to be joined depends on the temperature used and the distance of the hot plate from the fusion line. The higher the temperature of the hot plate and the closer it is to the fusion line, the shorter the time required to produce the melt. In one embodiment of the process, a surface of the hot plate touches the parts to be melted. In this embodiment, lower temperatures of the hot plate are sufficient to produce a melt. However, there is a risk that the molten material sticks to the hot plate and leaves residues on its surface. Therefore, in another embodiment of the process, the surface of the hot plate does not touch the parts to be melted, but keeps a distance from their surface. The distance generally is at least 0.1 mm; and it can be as large as 10 mm, or even more. In order to keep the time required for the melting process short, the distance generally is in the range of from 0.1 to 1.0 mm. Depending on the temperature of the hot plate and its distance from the fusion line, the residence time of the hot plate generally is in the range of from 1 to 60 seconds; e.g., 1 to 30 seconds; or even 1 to 15 seconds. The time required for the solidification of the melt after the parts have been joined generally is in the range of 10 to 60 seconds, for instance, 15 to 45 seconds.

In one embodiment of the process, the outer rim 23 of the end cap 20 and the upper rim of the collar 14 of the housing 10 are joined using a hot plate. In one embodiment, the outer rim 23 of the end cap 20 and the upper rim of the collar 14 of the housing 10 have the same width and the same outer diameter, i.e., they are congruent; and the upper rim of the collar 14 of the housing 10 is planar and the plane is perpendicular to the longitudinal axis of the housing 10. This greatly facilitates the joining process, as the surfaces of both parts will melt evenly, and a uniform, defect-free joint is formed when the two parts are pressed onto each other. A further advantage is that the collar 14 has a diameter which is larger than the diameter of the header section 12; and there is a gap between the upper rim of the collar 14 and the outside surface of the header section 12. This allows for heating and melting the upper rim of the collar 14 without also partially melting the outside surface of the header section 12. In a particular embodiment of the process, the outer rim 23 of the end cap 20 and the upper rim of the collar 14 of the housing 10 are heated by a hot plate having a temperature in the range of from 340 to 365° C.; and having a distance from the outer rim 23 of the end cap 20 and the upper rim of the collar 14, in axial direction, in the range of from 0.1 to 0.3 mm; for a time in the range of from 5 to 10 sec. The hot plate is removed and the outer rim 23 of the end cap 20 and the upper rim of the collar 14 of the housing 10 subsequently are pressed onto each other for a time in the range of from 20 to 30 sec.

LIST OF REFERENCE SIGNS

10 housing
11 tubular midsection
12 header section
13 nose
14 collar
15 fluid port
20 end cap
21 sealing face
22 nose
23 outer rim
24 annular plane
25 fluid port
26 two-start thread
30 diffusion and/or filtration device
31 internal chamber
32 bundle of hollow fiber membranes
33 end wall means

The invention claimed is:

1. A diffusion and/or filtration device comprising a housing comprising a tubular midsection; and header sections at both ends of the tubular midsection having a diameter larger than the diameter of the tubular midsection; characterized in that the wall strength of the header sections is greater than the wall strength of the tubular midsection; and a plurality of elongated noses is arranged on the inside surface of each the header sections, the noses running parallel to the longitudinal axis of the housing and parallel to each other, and one or more end caps having an inner surface which is axially symmetrical with regard to the longitudinal axis of the end cap and has an inner surface having the form of a funnel and comprising, in the direction of increasing diameter, a first section (I) taking the form of a cylinder or a truncated cone, a middle section (II) taking the form of a torus segment, and a third section (III) taking the form of a truncated cone, characterized in that the end cap comprises a circumferential planar sealing face sloping at an angle in the range of from about 5° to about 10° in a radial direction.

2. The diffusion and/or filtration device of claim 1, comprising:
   a) the housing, defining a longitudinally extending internal chamber including a first end and a second end;
   b) a bundle of semi-permeable hollow fiber membranes disposed within the internal chamber and extending longitudinally from the first end of the internal chamber to the second end of the internal chamber, the hollow fiber membranes each having an outer surface, and a first end and a second end corresponding to the first end and the second end of the internal chamber; c) end wall means supporting the first and second ends of the hollow fiber membranes within the internal chamber so as to sealingly separate the first ends and second ends of the hollow fiber membranes from the outer surfaces of the hollow fiber membranes between the first ends and second ends thereof; d) end caps sealing the mouths of the housing, wherein each end cap has an inner surface which is axially symmetrical with regard to the longitudinal axis of the end cap and has an inner surface having the form of a funnel and comprising, in the direction of increasing diameter, a first section (I) taking the form of a cylinder or a truncated cone, a middle section (II) taking the form of a torus segment, and a third section (III) taking the form of a truncated cone, characterized in that the end cap comprises a circumferential planar sealing face sloping at an angle in the range of from about 5° to about 10° in a radial direction.

3. The diffusion and/or filtration device of claim 2, wherein an upper rim of the header section of the housing slopes at the same angle as the circumferential planar sealing face of the end cap, the upper rim of the header section of the housing and the circumferential planar sealing face of the end cap contacting each other and forming a first tight seal; and an outer rim of the end cap being fused to the housing and providing a second tight seal.

4. The diffusion and/or filtration device of claim 3, wherein the outer rim of the end cap is fused to the upper rim of the collar of the housing to provide the second tight seal.

5. The diffusion and/or filtration device of claim 1, wherein the header sections each comprise a collar having a diameter which is larger than the diameter of the header section, an upper rim of the collar defining a gap to the outside surface of the header section, and being positioned below the upper rim of the header section.

6. A process for producing a diffusion and/or filtration device, comprising:
   a) providing a housing according to claim 1, the housing defining a longitudinally extending internal chamber including a first end and a second end;
   b) introducing a bundle of semi-permeable hollow fiber membranes each having an outer surface, a first end and a second end into internal chamber of the housing so that the bundle extends longitudinally from the first end of the internal chamber to the second end of the internal chamber; and the first ends and second ends of the hollow fiber membranes correspond to the first end and the second end of the internal chamber, respectively; c) providing end wall means supporting the first and second ends of the hollow fiber membranes within the internal chamber so as to sealingly separate the first ends and second ends of the hollow fiber membranes from the outer surface of the hollow fiber membranes between the first ends and second ends thereof, by introducing a potting material into the header sections of the housing and allowing the potting material to cure;
   d) opening the first and second ends of the hollow fiber membranes by cutting through the end wall means perpendicularly to the longitudinal axis of the housing;
   e) providing an end cap for each header section, wherein the end cap has an inner surface which is axially symmetrical with regard to the longitudinal axis of the end cap and has an inner surface having the form of a funnel and comprising, in the direction of increasing diameter, a first section (I) taking the form of a cylinder or a truncated cone, a middle section (II) taking the form of a torus segment, and a third section (III) taking the form of a truncated cone, characterized in that the end cap comprises a circumferential planar sealing face sloping at an angle in the range of from about 5° to about 10° in a radial direction;
   f) circumferentially beveling the wall of a rim of each header section to produce a rim of the header section sloping at an angle matching the slope of the circumferential planar sealing face of the end cap;
   g1) closing each header section with an end cap, thereby causing an upper rim of the header section of the housing and the circumferential planar sealing face of the end cap to contact each other and form a first tight seal;
   g2) fusing each end cap to the housing, thereby providing a second tight seal.

7. The process of claim 6, wherein the second tight seal is provided by fusing an outer rim of the end cap to the upper rim of the collar of the housing.

8. The process of claim 6, wherein a contact force is applied to the upper side of the end cap in the direction of the longitudinal axis of the housing, after the header section has been closed with the end cap, thereby pressing the circumferential planar sealing face of the end cap onto the upper rim of the header section of the housing; and the contact force is maintained until the end cap has been fused to the housing.

9. The process of claim 8, wherein the contact force is applied to an annular plane running along the circumference of the end cap on its upper side, the annular plane being perpendicular to the longitudinal axis of the end cap.

10. The process of claim 8, wherein the contact force is in the range of from about 3,000 to about 5,000 N.

11. The process of claim 7, wherein a contact force is applied to the upper side of the end cap in the direction of the longitudinal axis of the housing, after the header section has been closed with the end cap, thereby pressing the circumferential planar sealing face of the end cap onto the upper rim of the header section of the housing; and the contact force is maintained until the end cap has been fused to the housing.

12. The process of claim 9, wherein the contact force is in the range of from about 3,000 to about 5,000 N.

* * * * *